US008440612B2

(12) United States Patent
Greif et al.

(10) Patent No.: US 8,440,612 B2
(45) Date of Patent: May 14, 2013

(54) CONTROLLING GIARDIOSIS

(75) Inventors: Gisela Greif, Remagen (DE); Achim Harder, Koeln (DE); Thomas Bach, Wuppertal (DE); Gabriele Petry, Krefeld (DE); Eva-Maria Kruedewagen, Monheim (DE)

(73) Assignee: Bayer Intellectual Property GmbH (DE)

( * ) Notice: Subject to any disclaimer, the term of this patent is extended or adjusted under 35 U.S.C. 154(b) by 86 days.

(21) Appl. No.: 13/000,715

(22) PCT Filed: Jun. 20, 2009

(86) PCT No.: PCT/EP2009/004475
§ 371 (c)(1),
(2), (4) Date: Dec. 22, 2010

(87) PCT Pub. No.: WO2010/000399
PCT Pub. Date: Jan. 7, 2010

(65) Prior Publication Data
US 2011/0105388 A1 May 5, 2011

(30) Foreign Application Priority Data

Jul. 2, 2008 (DE) .......................... 10 2008 031 284

(51) Int. Cl.
*A61K 31/345* (2006.01)
*A61K 36/12* (2006.01)

(52) U.S. Cl.
USPC ......... 514/4.6; 514/21.1; 514/222.2; 514/449

(58) Field of Classification Search ........................ None
See application file for complete search history.

(56) References Cited

U.S. PATENT DOCUMENTS

| | | | |
|---|---|---|---|
| 3,262,930 A | 7/1966 | Herlinger et al. |
| 5,116,815 A | 5/1992 | Takagi et al. |
| 5,514,773 A | 5/1996 | Nishiyama et al. |
| 5,646,244 A | 7/1997 | Nishiyama et al. |
| 5,656,464 A | 8/1997 | Jeschke et al. |
| 5,663,140 A | 9/1997 | Scherkenbeck et al. |
| 5,717,063 A | 2/1998 | Scherkenbeck et al. |
| 5,747,448 A | 5/1998 | Ohyama et al. |
| 5,777,075 A | 7/1998 | Scherkenbeck et al. |
| 5,821,222 A | 10/1998 | Bonse et al. |
| 5,856,436 A | 1/1999 | Nishiyama et al. |
| 5,874,530 A | 2/1999 | Scherkenbeck et al. |
| 6,033,879 A | 3/2000 | Jeschke et al. |
| 6,329,338 B1 | 12/2001 | Sakanaka et al. |
| 6,369,028 B1 | 4/2002 | Scherkenbeck et al. |
| 2002/0035061 A1 | 3/2002 | Krieger et al. |
| 2008/0221222 A1 | 9/2008 | Greif et al. |

FOREIGN PATENT DOCUMENTS

WO WO 2006/053160 * 5/2006

OTHER PUBLICATIONS

Turrens et al. ("Inhibition of *Trypanosoma cruzi* and *T. brucei* NADH fumarate reductase by benznidazole and anthelmintic imidazole derivatives," Molecular and Biochemical Parasitology 82 (1996) 125-129).*
von Samson-Himmelstjerna et al. (In vivo activities of the new anthelmintic depsipeptide PF 1022A, Parasitol Res 86 (2000) 194-199).*
Moraes-Souza et al. ("Strategies for Prevention of Transfusion-Associated Chagas' Disease," Transfusion Medicine Reviews, X (1996) 161-170).*
Wolfe ("Giardiasis" Clin. Microbiol. Rev. 5 (1992) 93-100).*
Clark et al. ("Flagellated protozoan infections in turkeys," World Poultry 19 (2003) 1-4).*
Stockdale et al. ("Feline Trichomoniasis: An Emerging Disease?" Compendium Vet Jun. 2006 463-476).*
Petrin et al. (Clinical and Microbiological Aspects of *Trichomonas vaginalis*,) Clin Microbiol Rev 11 (1998) 300-317).*
Harder, A., et al., Chemotherapeutic approaches to protozoa: Haemosporina—Current Level of Knowledge and Outlook; Parasitol Res, 2001, (87): pp. 781-784.
Escobedo, A., et al., Giardiasis: A Pharmacotherapy Review; Expert Opin. Pharmacother., 8(12): pp. 1885-1902.
Raether, W., et al., Nitroheterocyclic Drugs with Broad Spectrum Activity; Parasitol Res. 2003, (90): pp. S19-S39.
Harder, A., et al., Mechanisms of Action of Emodepside: Parasitology Research: 2005. (97): pp. S1-S10.
Harder, A., et al., Chemotherapeutic Approaches to Protozoa: Giardia, Trichomonas and Entamoeba—Current Level of Knowledge and Outlook; Parasitol Res, 2001, (87): pp. 785-786.
Greif, G., et al., Chemotherapeutic Approach to Protozoa: Coccidiae—Current Level of Knowledge and Outlook; Parasitol Res, 2001, (87), pp. 973-975.
Harder, A., et al., Chemotherapeutic Approaches to Protozoa: Kinetoplastida—Current Level of Knowledge and Outlook; Parasitol Res, 2001, (87), pp. 778-780.
Harder, A., et al., Cyclootadepsipeptides—An Anthemintically Active Class of Compounds Exhibiting a Novel Mode of Action; International Journal of Antimicrobial Agents, 2003, (22), pp. 318-331.
Adam, R.D., Biology of Giardia Lamblia; Clinical Microbiology Reviews, Jul. 2001, pp. 447-475.
Marshall, M.M., Water Borne Protozoan Pathogens; Clinical Microbiology Reviews, Jan. 1997, vol. 10, No. 1. pp. 67-85.
Roxstroem-Lindquist, K., et al., Giardia Immunity—An Update; Trends in Parasitology, Jan. 2006, vol. 22, No. 1, pp. 26-31.
Huelsmeier, A.J., et al., Giardia Duodenalis: Direct Experimental Evidence for the Absence of a Glycosylphosphatidylinositol Anchor in a Variant Surface Protein; Experimental Parasitology,(2005), vol. 209, pp. 49-52.
Wright, J.M., et al., Efficacy of Antigiardial Drugs; Expert Opin. Drug Saf.; (2003). 2(6): pp. 529-541.
Monzote, L., A Review of Anti-Parasitic Patents (1988-2008); Recent Patents on Anti-Infective Drug Discovery, 2008, (3), pp. 177-191.
Eckmann, L., Mucosal Defences Against Giardia; Parasite Immunology, 2003, (25), pp. 259-270.
Hewlett, E., et al., Expertimental Infection of Mongrel Dogs With Giardia Lamblia Cysts and Cultured Trophozoites; The Journal of Infectious Diseases, Jan. 1982, vol. 115, No. 1, pp. 89-93.

(Continued)

*Primary Examiner* — Christina Bradley

(57) ABSTRACT

The present invention relates to the use of nifurtimox for the treatment of giardiosis, in particular in dogs and cats.

20 Claims, No Drawings

OTHER PUBLICATIONS

Abbitt, B., et al., Treatment of Giardiasis in Adult Greyhounds, Using Ipronidazole-Medicated Water; J. Amer. Vet. Med. Ass., 1936, (198), pp. 67-69.

Kirkpatrick, CE., et al., Feline Giardiasis, Observations on Natural and Induced infections; J. Amer. J. Vet Res., 1934, (45); Issue 10, pp. 2162-2188.

Ryan-Gullahorn, J., Giardia and Effective Cattery Management for the Veterinarian; Feline Practice, (2000), vol. 28, No. 2, pp. 8-9.

Zimmer, J.F., et al., Comparison of Four Protocols for the Treatment of Canine Giardiasis; Journal of the American Animal Hospital Association, (1986), vol. 22, pp. 168-172.

Mehlhorn, Giardiasis, Man; Encyclopedia Reference of Parasitology, Disease, Treatment, Therapy, (2001), Second Edition, Springer-Verlag, pp. 234-235.

McKellar, Q.A., et al., Veterinary Anthelminitics: Old and New; Trends in Parasitology; Elsevier Current Trends; (2004). vol. 20, No. 10, pp. 456-461.

PCT International Search Report Dated Oct. 13, 2009, 4 Pgs.

Zeledon, R.A., "Chapter 82 Hemoflagellates," 1996, Medical Microbiology, 4th edition, S. Baron, Editor. Galveston (TX): University of Texas Medical Branch at Galveston, 23 pages.

* cited by examiner

CONTROLLING GIARDIOSIS

The present invention relates to the use of nifurtimox for the treatment of giardiosis, in particular in dogs and cats.

The efficacy of nitro-heterocyclic compounds against protozoan diseases is known (1).

The Protozoa include single-nuclear organisms whose basic structure is a eukaryotic cell. The more precise systematics, however, reveal large differences in habit, morphology and the biochemical metabolism of the individual strains, classes, genera and species. This is why chemicals, depending on their target and active principle, usually do not act equally well against all Protozoa, but only against specific groups of Protozoa (2, 3, 4).

To date, the efficacy of nifurtimox has only been described against protozoan species of the genus *Trypanosoma*, e.g. *Trypanosoma brucei* and *Trypanosoma cruzi* (5). *Trypanosoma* have a flagellum which originates on the basal body ("kinetosome") and, in conjunction with the basal body, develops an undulating membrane. Parasites with this basic morphological type belong, within protozoan systematics, to the order Kinetoplastida. *Trypanosoma* grow predominantly in the blood plasma and are transmitted by blood-sucking arthropods. These pathogens cause Chagas disease ("trypanosomiasis") of humans. nifurtimox is currently almost the only compound which is active against these pathogens. This activity is probably based on inhibiting the enzyme trypanothione reductase, a specific trypanosomal enzyme. This enzyme is absent in other protozoan pathogens.

The activity of nifurtimox against Trichomonadida is described in a patent application filed in parallel.

Giardiosis is an infectious disease which is caused by flagellated, unicellular parasites of the genus *Giardia*. This genus belongs to the order Diplomonadida. Its most important representative is *Giardia lamblia* (syn. *Giardia intestinalis*, *Giardia duodenalis*). The percentage of positive dog and cat samples is up to 50% worldwide, and 2-7% in Central Europe. Infection leads to persistent diarrhoea and in some cases bloody faeces, caused by inflammation of the duodenum and jejunum, especially in very young animals up to half a year old. Chronic disease can lead to presently delayed growth (6).

More than 7 genotypes (A-G) have been described for *Giardia* isolates. Genotypes A+B are infectious for humans and may also occur in cats, dogs, beavers, sheep, calves, horses, pigs and monkeys. This is why the disease is considered to be a "zoonosis": Humans can become infected with cysts from dogs and cats via contaminated drinking water. *Giardia* infections are worldwide among the most frequent causative agents of what are known as water-borne outbreaks in humans (7).

Infection is usually via the cyst form by the oral route, by contaminated drinking water or infectious faeces. In the gut, so-called trophozoites hatch from the cyst. A trophozoite measures 11-17×7-11 μm, contains two nuclei and 8 flagella. In contrast to other groups of flagellated parasites, *Giardia* trophozoites do not penetrate intracellularly into epithelia. Trophozoites have an acetabulum, with the aid of which they can anchor themselves on the outside of the gut lumen of humans, monkeys, pigs, dogs and cats, where they multiply by division. Massive attack blocks and modifies the absorbing gut surface and in some cases causes bloody diarrhoea. Cysts are again formed in the appendix and are again excreted via the faeces with a prepatency time of 5-16 days after the primary infection. Cysts can be excreted over a period of 4-5 weeks and remain infectious over several weeks (8, 9).

There are substantial morphological and biochemical differences to the order Kinetoplastida: Diplomonadida have 8 flagella and two nuclei, but there are no mitochondria and no Golgi complex, and no intracellular stages are known during the life cycle. In contrast to *Trypanosoma*, surface proteins of *Giardia* do not have a GPI anchor (10).

In dogs and cats, a therapy with metronidazole (Clont®, Flagyl®, Elyzol®) at a dosage of 12.5-22 mg/kg bodyweight b.i.d. over 5 days is currently recommended. (11): Metronidazole and other 5-nitroimidazoles are activated by the enzyme pyruvate-ferredoxin oxidoreductase to form free nitro radicals, which then engage with the parasite DNA metabolism. This is why ipronidazole (Ipropan®, 126 mg/l drinking water over 7 days) and tinidazole (Fasigyn®, 44 mg/kg bodyweight over 3 days) are also suitable for the therapy of giardiosis in dogs (12, 13).

Substances which are recommended from the group of the benzimidazoles are mebendazole, albendazole or fenbendazole (oral over 3 days). Benzimidazoles interfere with the polymerization of the microtubuli by binding to the subunit of β-tubulin. Microtubuli are important cytoskeleton elements of the parasite which stabilize in a particular manner the acetabulum of the trophozoites.

Substances which are employed in the human sector include antibiotics (for example paramomycin, 25-35 mg/kg/day in three dosages for 7-10 days), quinacrin and furazolidon (100 mg t.i.d. 7 days long) or nitazoxanid (500 mg b.i.d. for 3 days) (14).

Many of these classes of active substances have been employed for a long time for the treatment of giardiosis, and the development of resistance has been detected for most and has lead to documented failures in the treatment. The development of novel active substances and treatment concepts is therefore a necessity (15).

Surprisingly, we have now found that nifurtimox has an activity against *Giardia* species. This activity has not been described to date. The activity is directed at the gut-pathogenic stages and prevents cyst formation.

The invention therefore relates to:
the use of nifurtimox for the preparation of pharmaceuticals for the treatment of disease caused by *Giardia* species.
nifurtimox is the compound of the formula (I):

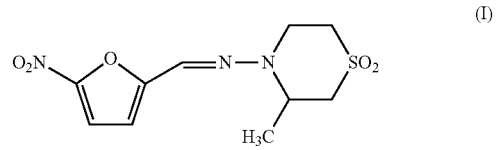 [SMILES: CC1CS(=O)(=O)CCN1N=Cc1ccc([N+](=O)[O-])o1]

If appropriate, the use in the form of customary pharmaceutically acceptable salts is also suitable. If appropriate, the use of hydrates or other solvates of the active substances or, if appropriate, of their salts is furthermore also suitable.

The use can be both prophylactic and therapeutic. The activity is directed against different stages of the pathogen; in particular, nifurtimox acts against the gut-pathogenic stages and prevents cyst formation.

Of particular importance among the *Giardia* species are *Giardia lamblia* (syn. *Giardia intestinalis, Giardia duodenalis*), *Giardia bovis* and *Giardia caprae*. The species listed here are frequently used synonymously for one another and display little host specificity.

Organisms which are treated in accordance with the invention are animals (carnivores and wild animals), preferably mammals such as, for example, horses, pigs, rabbits, in particular dogs or cats.

According to one embodiment, the preferred treatment among mammals is the treatment of wild animals and in particular of carnivores (dogs, cats).

Humans, too, are suitable for treatment, since humans can become infected with the animal-pathogenic *Giardia* species via contaminated drinking water.

Giardiosis is found mainly in young animals, preferably aged 3-10 weeks, and causes severe diarrhoea and reduced weight gain.

The active substances are applied directly or in the form of suitable preparations via the enteral, parenteral, dermal route.

The enteral administration of the active substances is effected for example orally in the form of powders, suppositories, tablets, capsules, pastes, drinks, granules, drenches, boluses, medicated feed or drinking water. Dermal administration is effected for example in the form of dipping, spraying, bathing, washing, pouring on and spotting on and dusting. Parenteral administration is effected for example in the form of an injection (intramuscular, subcutaneous, intravenous, intraperitoneal) or by implants.

Suitable preparations are:
solutions such as solutions for injection, oral solutions, concentrates for oral administration after dilution, solutions for use on the skin or in body cavities, pour-on and spot-on formulations, gels;
emulsions and suspensions for oral or dermal administration and for injection; semi-solid preparations;
formulations in which the active substance is incorporated in an ointment base or in an oil-in-water or water-in-oil emulsion base;
solid preparations such as powders, premixes or concentrates, granules, pellets, tablets, boluses, capsules; aerosols and inhalers, active-substance-containing shaped articles.

Solutions for injection are administered for example intravenously, intramuscularly and subcutaneously.

Oral solutions are administered directly. Concentrates are administered orally after previously having been diluted to the use concentration.

Solutions for use for application to the skin are trickled on, painted on, rubbed on, splashed on, sprayed on or applied by dipping, bathing or washing.

Gels are applied to or painted onto the skin or introduced into body cavities.

Pour-on and spot-on formulations are poured onto or spotted onto limited areas of the skin, the active substance either penetrating the skin and acting systemically or distributing on the body surface.

Emulsions are either of the water-in-oil type or of the oil-in-water type and can be applied orally, dermally or as injections.

Suspensions can be applied orally, dermally or as an injection.

Semi-solid preparations can be administered orally or dermally. They differ from the above-described suspensions and emulsions merely by the fact that they are more viscose.

To prepare solid preparations, the active substances are mixed with suitable carriers, if appropriate with addition of adjuvants, and formulated as desired.

Especially preferred in accordance with the invention is oral administration, and tablets are especially preferred among the usual oral use forms.

All the abovementioned pharmaceutical forms, the additives and adjuvants to be used and the preparation of these pharmaceutical forms are known in principle to the skilled worker.

The active substances can exist in combination with synergists or with further active substances. Further active substances which may be mentioned are:

Coccidiostats such as robenidine or amprolium, in some cases in combination with folic acid antagonists (for example pyrimethamin, epiroprim, trimetoprim); antibiotics such as, for example clindamycin, paramomycin or spiramycin; sulfonamides such as, for example, sulfadimethoxin, sulfadimidin, sulfadiazin; anthelmintics such as, for example, cyclic depsipeptides (for example emodepside, PF1022A), amidine derivatives (tribendimidine, amidantel, bay d 9216), praziquantel or benzyl benzoate.

For a long-time treatment effect, it is recommended to, disinfect regularly as part of the animal-keeping routine.

Anthelmintics, in particular cyclic octadepsipeptides such as PF1022A or emodepside are suitable for controlling nematode infections in humans and animals (16). Here, all economically important nematodes in the gastrointestinal tract, including in dogs, are destroyed. It is also known that, in the case of nontreatment of the animals, the immune response (GALT=gut-associated-lymphoid-tissue) is directed against the worms (17). This is called the Th2 response of the immune system. In the case of noninfection, the immune response is normally balanced, i.e. the antagonist of the Th2 response, which is called the Th1 response, which is directed against Protozoa, viruses and bacteria, is just as pronounced as the Th2 response.

If an infection with nematodes, for example an infection with hookworm, roundworm or whipworm, is present in the animal in question, for example in the dog, then the balance is adversely affected, and the result is a predominant protozoan infection in the gut, caused, for example, by *Giardia* species. If the nematode infection is now overcome by suitable anthelmintics, the defense against *Giardia* species is enhanced indirectly, by allowing the Th1 response to act against these Protozoa. In the combination nifurtimox plus anthelmintics, the nifurtimox will now be able to exert better control of the *Giardia* infection, since the latter is already partly contained as the result of the Th1 response, which is indirectly enhanced as the result of the nematode control, i.e. the number of parasites in the gut is already reduced.

In accordance with the preferred embodiment, nifurtimox is employed in combination with anthelmintics.

Anthelmintics which are preferably employed are 24-membered cyclodepsipeptides (cyclooctadepsipeptides). The following may be mentioned:

Compounds of the Formula (IIa)

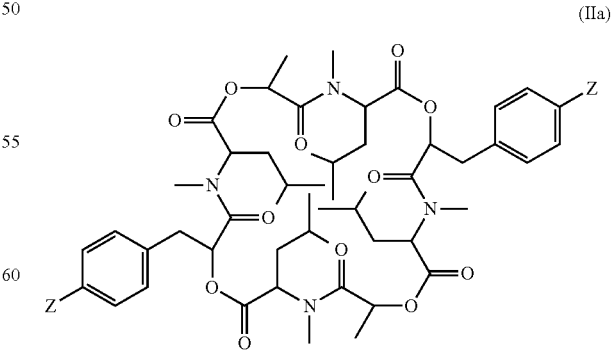

in which
Z represents hydrogen, N-morpholinyl, $NH_2$, mono- or dimethylamino.

Moreover, compounds of the following formula (IIb) may be mentioned:

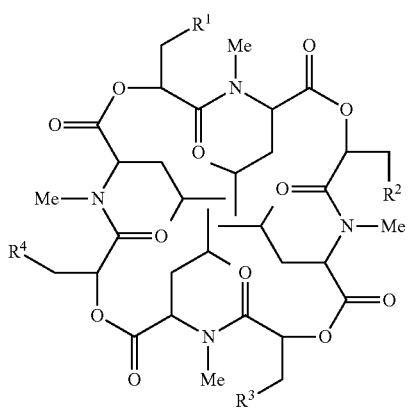

(IIb)

in which $R^1, R^2, R^3, R^4$ independently of one another represent hydrogen, $C_1$-$C_{10}$-alkyl or aryl, in particular phenyl, which are optionally substituted by hydroxyl, $C_1$-$C_{10}$-alkoxy or halogen.

The compounds of the general formula (IIb) are known and can be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

The cyclic depsipeptides with 24 ring atoms also include compounds of the general formula (IIc)

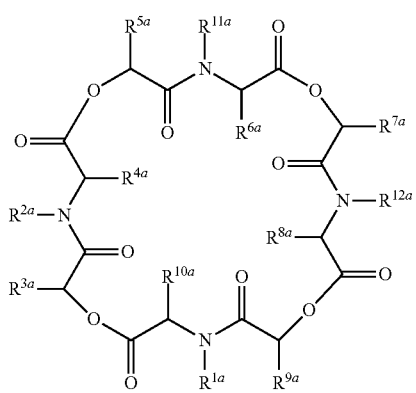

(IIc)

in which $R^{1a}, R^{2a}, R^{11a}$ and $R^{12a}$ independently of one another represent $C_{1-8}$-alkyl, $C_{1-8}$-haloalkyl, $C_{3-6}$-cycloalkyl, aralkyl, aryl, $R^{3a}, R^{5a}, R^{7a}, R^{9a}$ independently of one another represent hydrogen or a straight-chain or branched $C_{1-8}$-alkyl, each of which can optionally be substituted by hydroxyl, $C_{1-4}$-alkoxy, carboxyl,

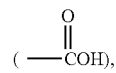

carboxamide,

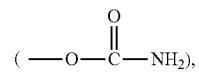

imidazolyl, indolyl, guanidino, —SH or $C_{1-4}$-alkylthio, and which furthermore represent aryl or aralkyl, each of which can be substituted by halogen, hydroxyl, $C_{1-4}$-alkyl, $C_{1-4}$-alkoxy, $R^{4a}, R^{6a}, R^{8a}, R^{10a}$ independently of one another represent hydrogen, straight-chain $C_{1-5}$-alkyl, $C_{2-6}$-alkenyl, $C_{3-7}$-cycloalkyl, each of which can optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl, each of which can be substituted by halogen, hydroxyl, $C_{1-4}$-alkyl, $C_{1-4}$-alkoxy, and their optical isomers and racemates.

Preferred compounds of the formula (IIc) are those in which $R^{1a}, R^{2a}, R^{11a}$ and $R^{12a}$ independently of one another represent methyl, ethyl, propyl, isopropyl, n-, s-, t-butyl or phenyl, each of which is optionally substituted by halogen, $C_{1-4}$-alkyl, OH, $C_{1-4}$-alkoxy, and represent benzyl or phenylethyl, each of which can optionally be substituted by the radicals mentioned for phenyl;

$R^{3a}$ to $R^{10a}$ have the abovementioned meanings.

Especially preferred compounds of the formula (IIc) are those in which $R^{1a}, R^{2a}, R^{11a}$ and $R^{12a}$ independently of one another represent methyl, ethyl, propyl, isopropyl or n-, s-, t-butyl, $R^{3a}, R^{5a}, R^{7a}, R^{9a}$ represent hydrogen, straight-chain or branched $C_{1-8}$-alkyl, in particular methyl, ethyl, propyl, i-propyl, n-, s-, t-butyl, each of which can optionally be substituted by $C_{1-4}$-alkoxy, in particular methoxy, ethoxy, imidazolyl, indolyl or $C_{1-4}$-alkylthio, in particular methylthio, ethylthio, furthermore represent phenyl, benzyl or phenethyl, each of which can optionally be substituted by halogen, in particular chlorine.

$R^{4a}, R^{6a}, R^{8a}, R^{10a}$ independently of one another represent hydrogen, methyl, ethyl, n-propyl, n-butyl, vinyl, cyclohexyl, each of which can optionally be substituted by methoxy, ethoxy, imidazolyl, indolyl, methylthio, ethylthio, furthermore represent isopropyl, s-butyl, and furthermore represent optionally halogen-substituted phenyl, benzyl or phenylethyl.

The compounds of the formula (IIc) can also be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

A very especially preferred depsipeptide which may be mentioned is the compound PF 1022, which is known from EP-A 382 173; it is the compound of the formula (IIa) in which both substituents Z represent hydrogen. PF 1022 therefore has the following formula (IId):

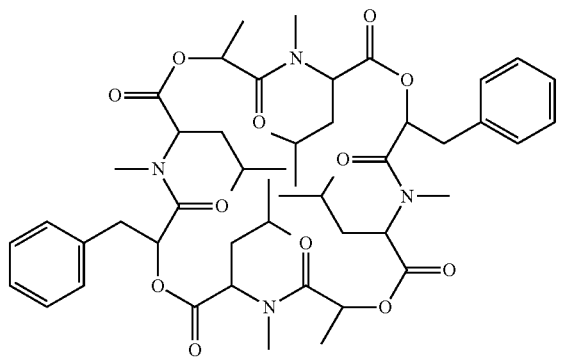

(IId)

Further preferred depsipeptides are compounds which are disclosed in the PCT application WO 93/19053, which are compounds of the formula (IIa)
in which
Z represents N-morpholinyl, $NH_2$, mono- or dimethylamino.

Very especially preferred among these compounds is the depsipeptide emodepside (PF 1022-221). This is the compound of the formula (IIa) in which both radicals Z represent the morpholinyl radical. The INN emodepside represents the compound with the systematic name: cyclo[(R)-lactoyl-N-methyl-L-leucyl-(R)-3-(p-morpholinophenyl)lactoyl-N-methyl-L-leucyl-(R)-lactoyl-N-methyl-L-leucyl-(R)-3-(p-morpholinophenyl)lactoyl-N-methyl-L-leucyl. Emodepside is described in WO 93/19053 and has the following formula:

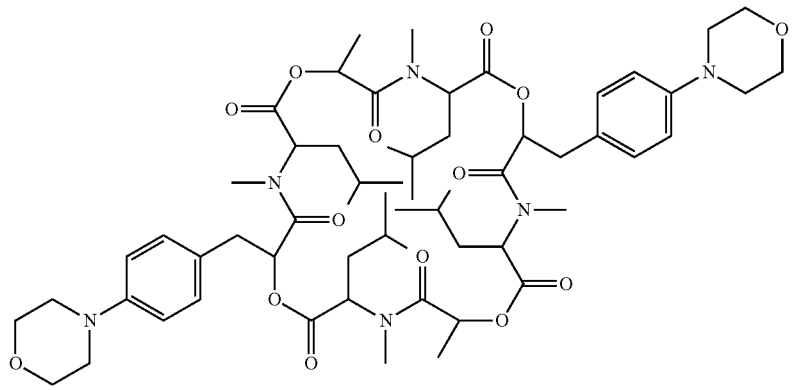 [SMILES: CC(C)CC1C(=O)OC(Cc2ccc(N3CCOCC3)cc2)C(=O)N(C)C(CC(C)C)C(=O)OC(C)C(=O)N(C)C(CC(C)C)C(=O)OC(Cc2ccc(N3CCOCC3)cc2)C(=O)N(C)C(CC(C)C)C(=O)OC(C)C(=O)N1C]

Depending on their structure, the abovementioned active substances which are suitable for the combination may be present in stereoisomeric forms or as stereoisomers, for example as enantiomers or racemates. Both the stereoisomer mixtures and the pure stereoisomers can be used in accordance with the invention.

The following may furthermore optionally be used: salts of the active substances with pharmaceutically acceptable acids or bases, and also solvates, in particular hydrates, of the active substances or of their salts.

Use in combination means either that nifurtimox and the second active substance, in particular a cyclodepsipeptide, can be employed separately or staggered. In this case, nifurtimox and the second active substance are formulated as a separate pharmaceutical.

The simultaneous use is also feasible. According to a use form which is suitable for this case, the active substances of the combination are formulated together in one composition.

Ready-to-use preparations usually contain the active substance in question in concentrations of 10 ppm to 20% by weight, preferably from 0.1 to 10% by weight.

Preparations which are diluted prior to use contain the active substance in question in concentrations of from 0.5 to 90% by weight, preferably from 5 to 50% by weight. In concentrated solutions for metering into the drinking water, the active substance in question is present for example in concentrations of from 0.5 to 20% by weight, preferably 1 to 15% by weight, especially preferably 2 to 10% by weight.

In general, it has proved advantageous to administer amounts of from approximately 0.05 to approximately 400 mg, preferably from 0.1 to 200 mg, of active substance per kg body weight per day in order to achieve effective results.

In the mixture with other coccidiostats, antibiotics or anthelmintics, the active substances according to the invention are present in the ratio 1 to 0.01-50 up to 1 to 1-50.

The active substances can also be administered together with the animals' feed or drinking water.

Feed and foodstuffs contain 0.005 to 1000 ppm, preferably 0.05 to 500 ppm, of the active substance in combination with a suitable edible material.

Such a feed and foodstuff can be used both for therapeutic and for prophylactic purposes.

A disinfectant may be employed to complement the nifurtimox. The disinfectant is used to disinfect the locations where the animals (or the humans) are during the treatment. The disinfectant takes care of the elimination of the parasitic persistent stages, preferably by destroying the cyst forms which are excreted, and thereby prevents reinfection after the end of the treatment. The disinfectant can therefore already be employed before the treatment with nifurtimox; as a rule, however, it is better to employ it at the same time, as, or at least before finishing, the treatment with nifurtimox.

Examples of disinfectants are those based on biocidal phenols and/or phenol derivatives. Biocidal phenols are understood as meaning those phenol compounds which bear a free OH group and have a biocidal activity. These phenols can bear further ring substituents such as, for example, halogens, in particular chlorine, $C_{1-6}$-alkyl, $C_{3-6}$-cycloalkyl, phenyl, chlorophenyl, benzyl and/or chlorobenzyl.

Examples of non-chlorinated biocidal phenols are; 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-propyl phenol, 4-n-butylphenol, 4-n-amylphenol, 4-n-hexylphenol, thymol (5-methyl-2-isopropylphenol), 2-phenylphenol, 4-phenylphenol, 2-benzylphenol. A non-chlorinated biocidal phenol which is preferably employed is 2-phenylphenol.

Examples of chlorinated biocidal phenols are 4-chloro-3-methylphenol (PCMC, p-chloro-m-cresol), 4-chloro-3-ethylphenol, 2-n-amyl-4-chlorophenol, 2-n-hexyl-4-chlorophenol, 2-cyclohexyl-4-chlorophenol, 4-chloro-3,5-xylenol (PCMX, p-chloro-m-xylenol), 2,4-dichloro-3,5-xylenol (DCMX, dichloro-p-xylenol), 4-chloro-2-phenylphenol, 2-benzyl-4-chlorophenol, benzyl-4-chloro-m-cresol, 4-chlorobenzyldichloro-m-cresol. Preferred chlorinated biocidal phenols are 2-benzyl-4-chlorophenol, 4-chloro-3,5-xylenol, 2,4-dichloro-3,5-xylenol and, in particular, 4-chloro-3-methylphenol.

In the present context, phenol derivatives are understood as meaning phenol-derived compounds whose OH group is derivatized, so that they do not contain any free OH groups. They are preferably phenol ethers, in particular those with aliphatic alcohols having 1 to 6 carbon atoms. Phenoxyethanol may be mentioned by way of preferred example.

It is preferred to employ the disinfectants described in WO 2007/009606, which contain biocides and a keratolytic agent. Suitable biocides or biocide combinations and suitable keratolytic agents are described in detail in WO 2007/009606, to which document express reference is made.

EXAMPLES

Formulation Examples

Example 1

Liquid Formulation

Suspensions in 100 ml glycerine formal/glycerine polyethylene glycol ricinoleate (Cremophor® EL)/water in the mixing ratio of 1:10 together with:
500 mg nifurtimox
1000 mg nifurtimox

Example 2

Liquid Formulation

Suspensions in 100 ml Cremophor® EL/water in the mixing ratio 1:5 together with
500 mg nifurtimox
1000 mg nifurtimox

Example 3

Solid Formulation

The active substances in the amounts detailed hereinbelow are filled into a gelatine capsule in the form of a powder:
250 mg nifurtimox

Example 4

Tablet nifurtimox tablets are known and commercially available as a pharmaceutical for example under the trade name Lampit®.

Biological Examples

Example 1

Beagle puppies aged 10-11 weeks which had 11 days to settle in the animal centre before being infected were infected orally with 50 000 *Giardia duodenalis* cysts. The cysts for the infection were obtained with the aid of a sucrose gradient from the faeces of dogs which excreted *Giardia* cysts and stored at 4 degrees centigrade in Bacto-Casitone medium for no longer than 2 weeks. From day 10 after the infection, the puppies were kept in individual cages in order to collect the daily total faeces for each individual. The quantitative determination of the cyst excretion was performed in the 4 days prior to treatment (day −3 to 0), and the puppies were divided randomly into two groups, taking into consideration the cyst excretion. On day 0, the 7 puppies of the treatment group were treated once with an oral dose of 50 mg/kg nifurtimox (Lampit®), while the 6 dogs of the control group remained untreated. The quantitative determination of the cyst excretion was continued from day 1 to day 8 after the treatment.

Results: The activity was calculated using the following formula:

$$\text{Activity }\% = \frac{\text{number of cysts in the control group} - \text{number of cysts in the treatment group}}{\text{number of cysts in the control group}} \times 100$$

The calculated activity upon a single nifurtimox dose was 90.4% (see Table 1).

Method: The quantitative determination of the cyst excretion was performed using a modified version of Hewlett (18): 4 g faeces were dissolved in 100 ml of water, sieved and allowed to sediment. The sediment was applied to a 1 M sucrose gradient (specific gravity 1.13), and the cysts, which were concentrated at the sucrose/water boundary layer after the centrifugation were pipetted off. After a wash step followed by centrifugation, the cysts in the pellet were counted. To this end, an aliquot of the pellet was counted under the microscope, and the number of cysts per g faeces was calculated.

TABLE 1

| Giardia cyst excretion before and after treatment with nifurtimox | | | | | | | | | | | | |
|---|---|---|---|---|---|---|---|---|---|---|---|---|
| Dog | D−3 | D−2 | D−1 | D0 | D1 | D2 | D3 | D4 | D5 | D6 | D7 | D8 |
| 50 mg/kg nifurtimox on day D0 | | | | | | | | | | | | |
| 9048 | 22402 | 186750 | 189275 | 19681 | 0 | 0 | 0 | 424 | 0 | 0 | 191 | 1621 |
| 9028 | 5259 | 45672 | 45725 | 16419 | 2636 | 180 | 224 | 1451 | 1318 | 4102 | 4615 | 1768 |
| 8343 | 5339 | 28322 | 26163 | 13644 | 2391 | 0 | 0 | 193 | 153 | 6315 | 223 | 508 |
| 8329 | 29625 | 907 | 1306 | 4397 | 504 | 0 | 0 | 590 | 1700 | 3693 | 8881 | 3294 |
| 9040 | 1063 | 923 | 14238 | 8456 | 4928 | 0 | 0 | 0 | 1094 | 2000 | 431 | 517 |

TABLE 1-continued

Giardia cyst excretion before and after treatment with nifurtimox

| | | | | | | | | | | | | | |
|---|---|---|---|---|---|---|---|---|---|---|---|---|---|
| 9038 | 1385 | 5897 | 2264 | 0 | 152 | 0 | 0 | 0 | 0 | 1201 | 1873 | 14181 | |
| 9020 | 3263 | 905 | 788 | 375 | 0 | 0 | 0 | 652 | 137 | 353 | 608 | 0 | |
| Σ | 9762 | 38482 | 39966 | 8996 | 1516 | 26 | 32 | 473 | 629 | 2523 | 2403 | 3127 | |

Infected, untreated control

| | | | | | | | | | | | | | |
|---|---|---|---|---|---|---|---|---|---|---|---|---|---|
| 9008 | 65325 | 41925 | 368 | 0 | 450 | 179 | 1183 | 3288 | 4747 | 14232 | 22237 | 3684 | |
| 8341 | 21150 | 44988 | 35525 | 3138 | 1332 | 806 | 23399 | 17739 | 27253 | 9321 | 2660 | 12901 | |
| 8309 | 7144 | 34613 | 33688 | 4531 | 25050 | 13238 | 5547 | 26106 | 52000 | 5125 | 47365 | 47999 | |
| 8327 | 21250 | 21485 | 1350 | 3991 | 5383 | 4520 | 3529 | 17355 | 6145 | 14298 | 25331 | 110846 | |
| 8313 | 2975 | 3185 | 8168 | 1209 | 609 | 6133 | 8438 | 6739 | 18113 | 4027 | 7103 | 2645 | |
| 9026 | 945 | 2813 | 1723 | 2038 | 3544 | 3366 | 20163 | 11291 | 6719 | 4621 | 5867 | 5621 | |
| Σ | 19798 | 24835 | 13470 | 2485 | 6061 | 4707 | 10377 | 13753 | 19163 | 8604 | 184427 | 30616 | |

| | Σ Giardia cyst excretion | | |
|---|---|---|---|
| Treatment | Day −3 to 0 | Day 1 to 8 | Activity |
| 50 mg/kg nifurtimox | 24302 | 1341 | 90.4% |
| Infected, untreated control | 15147 | 13963 | — |

D−3 to D−1: Days before the treatment
D0: Day of treatment
D1 to D8: Days after the treatment Example 2

Beagle puppies aged 11-15 weeks which had at least 2 weeks to settle in the animal centre before being infected were infected orally with 50 000 *Giardia duodenalis* cysts before the beginning of the study. The cysts for the infection were obtained with the aid of a sucrose gradient from the faeces of dogs which excreted *Giardia* cysts and stored at 4 degrees centigrade in Bacto-Casitone medium for no longer than 2 weeks. 18 puppies which excreted *Giardia* cysts were included in the study and kept in individual cages in order to collect the daily total faeces. The quantitative determination of the cyst excretion was performed as an experiment 145.717, with the modification that the aliquot of the pellet was counted under the microscope with the aid of a Fuchs-Rosenthal hematocytometer. The quantitative determination of the cyst excretion was performed for 4 days before the treatment (day −3 to 0), and the puppies were divided randomly into three groups, taking into consideration the cyst excretion. On three successive subsequent days (day 0, 1 and 2), the 6 puppies of treatment group 1 were treated in the morning with an oral dose of 50 mg/kg nifurtimox (Lampit®), while the dogs of treatment group 2 were treated on these three days in the morning with an oral dose of 50 mg/kg fenbendazole (fenbendazole tablets). The 6 dogs of the control group remained untreated. The quantitative determination of the cyst excretion was continued from day 1 to day 8 after the treatment.

Results: The calculated activity of nifurtimox was 98.6%, while the activity of fenbendazole was 48.3% (see Table 2).

TABLE 2

Giardia cyst excretion before and after treatment with nifurtimox in comparison with the treatment with fenbendazole.

| Dog | D−3 | D−2 | D−1 | D0 | D1 | D2 | D3 | D4 | D5 | D6 | D7 | D8 |
|---|---|---|---|---|---|---|---|---|---|---|---|---|
| 50 mg/kg nifurtimox on days D0, D1 and D2 | | | | | | | | | | | | |
| 9300 | 63463 | 79689 | 91293 | 103442 | 1261 | 527 | 0 | 0 | 0 | 0 | 0 | 903 |
| 0136 | 102900 | 68914 | 59273 | 112084 | 2000 | 0 | 0 | 622 | 1299 | 93 | 0 | 0 |
| 0116 | 57571 | 10685 | 25515 | 60420 | 809 | 741 | 0 | 0 | 229 | 0 | 0 | 517 |
| 8553 | 40909 | 8278 | 3472 | 675 | 187 | 0 | 0 | 185 | 0 | 98 | 0 | 0 |
| 8531 | 4891 | 1618 | 37203 | 89880 | 974 | 0 | 0 | 0 | 0 | 0 | 87 | 975 |
| 0134 | 28773 | 133 | 8528 | 86 | 0 | 0 | 0 | 0 | 2299 | 1842 | 237 | 0 |
| Σ | 49751 | 28220 | 37547 | 61098 | 872 | 211 | 0 | 135 | 638 | 339 | 54 | 399 |
| 50 mg/kg fenbendazole on days D0, D1 and D2 | | | | | | | | | | | | |
| 0117 | 18781 | 47754 | 243143 | 49400 | 67200 | 0 | 67109 | 49423 | 3116 | 4635 | 17474 | 0 |
| 9320 | 60193 | 23808 | 56014 | 28559 | 14596 | 5980 | 7043 | 652 | 18725 | 7546 | 20780 | 5555 |
| 8555 | 44218 | 26526 | 2349 | 639 | 872 | 0 | 961 | 0 | 4432 | 5594 | 260 | 5968 |
| 8543 | 34119 | 18113 | 16328 | 2719 | 12488 | 3386 | 3075 | 12038 | 0 | 3691 | 18056 | 10875 |
| 0135 | 20463 | 7230 | 14744 | 17037 | 6178 | 490 | 0 | 0 | 0 | 0 | 251 | 0 |
| 9328 | 2003 | 10109 | 21360 | 23290 | 723 | 552 | 5388 | 14133 | 19057 | 11495 | 20657 | 6370 |
| Σ | 29963 | 22257 | 58990 | 20274 | 17010 | 1735 | 13929 | 12781 | 7555 | 5494 | 12913 | 4795 |
| Infected, untreated control | | | | | | | | | | | | |
| 0121 | 112757 | 27324 | 121092 | 108868 | 153336 | 64620 | 6127 | 190 | 6879 | 85408 | 73978 | 50256 |
| 0138 | 22125 | 65547 | 60200 | 26964 | 22234 | 855 | 17893 | 8138 | 13204 | 3681 | 439 | 1470 |
| 9332 | 22346 | 34475 | 42076 | 24466 | 24360 | 19145 | 12575 | 1455 | 5712 | 16122 | 21440 | 12563 |
| 8529 | 8884 | 49213 | 12881 | 32105 | 71378 | 1139 | 6409 | 4739 | 5297 | 23725 | 11626 | 2835 |

TABLE 2-continued

Giardia cyst excretion before and after treatment with nifurtimox in comparison with the treatment with fenbendazole.

| 9330 | 18829 | 4711  | 22120 | 2476  | 1987  | 0     | 246   | 2492 | 4472 | 602    | 2052  | 813   |
|------|-------|-------|-------|-------|-------|-------|-------|------|------|--------|-------|-------|
| 0137 | 4623  | 12238 | 14406 | 14328 | 2134  | 10156 | 16756 | 0    | 8170 | 104020 | 79097 | 55935 |
| Σ    | 31594 | 32251 | 45463 | 34868 | 45905 | 15986 | 10001 | 2836 | 7289 | 38926  | 31439 | 20645 |

| | Σ Giardia cyst excretion | | |
|---|---|---|---|
| Treatment | Day: −3 to 0 | Day 3 to 8 | Activity |
| 50 mg/kg nifurtimox | 44154 | 261 | 98.6% |
| 50 mg/kg fenbendazole | 32871 | 9578 | 48.3% |
| Infected, untreated control | 36044 | 18523 | — |

D−3 to D−1: Days before the treatment
D0, D1, D2: Days of treatment
D3 to D8: Days after the treatment References
(1) Raether w., Hänel H. (2003): Nitroheterocyclic drugs with broad spectrum activity Parasitol Res. 90:S19-S39.
(2) Harder A. Greif G, Haberkorn A. (2001a): Chemotherapeutic approaches to protozoa: Haemosporina—current level of knowledge and outlook.
(3) Harder A, Greif G., Haberkorn A. (2001b): Chemotherapeutic approaches to protozoa: Giardia, Trichomonas and Entamoeba—current level of knowledge and outlook.
(4) Greif G, Harder A, Haberkorn A (2001): chemotherapeutic approaches to protozoa: Coccidia—current level of knowledge and outlook.
(5) Harder A, Greif G., Haberkorn A (2001c): Chemotherapeutic approaches to protozoa: Kinetoplastida—current level of knowledge and outlook. Parasitol Res 87:778-780.
(6) Adam R. D. (2001): Biology of Giardia lamblia. Clinical Microbiology Reviews, July: 447-475.
(7) Marshall M M, Naumovitz D., Ortega Y., Sterling C R. (1997): Waterborne protozoan Pathogens. Clinical Microbiology Reviews January:67-85.
(8) Roxström-Lindquist, K. Palm D., Reiner D., Ringqvist E., Svärd S G. (2006): Giardia immunity—an update. Trends in Parasitology Vo. 22(1):26-31.
(9) Beckmann L. (2003): Mucosal defenses against Giardia. Parasite Immunology 25:259-270.
(10) Hülsmeier A. J., Köhler P. (2005): Giardia duodenalis: direct experimental evidence for the absence of a glycosylphosphatidylinositol anchor in a variant surface protein. Experimental Parasitology 109:49-52.
(11) Kirkpatrick, C E, Farrell J P (1984): Feline giardiasis: observations on natural and induced infections. Amer. J. Vet. Res. 45:2182-2188.
(12) Zimmer J F, Burrington D B (1986): Comparison of four protocols for the treatment of canine giardiasis. J. Amer. Anim. Hosp. Ass. 22:168-172.
(13) Abbitt B, Huey R L, Eugster A K, Syler J. (1986): Treatment of giardiasis in adult greyhounds, using ipronidazole-medicated water. J. Amer. Vet. Med. Ass. 188:67-69.
(14) Wright J M., Dunn L. A., Uperoft P., Uperoft J. A. (2003): Efficacy of antigiardial drugs. Expert Opin. Drug Saf. 2(6): 529-541.
(15) Escobedo A. A & Cimerman S. (2007): Giardiasis: a pharmacotherapy review. Expert Opin. Pharmacother. 8(12):1885-1902.
(16) Harder A. et al. (2003) Cyclooctadepsipeptides—an anthelmintically active class of compounds exhibiting a novel mode of action. Int. J. Antimicrobial Agents. 22: 318-331.
(17) Mehlhorn (ed) (2001) Giardiasis, Man; Encyclopedic Reference of Parasitology, Diseases, treatment, Therapy, Second Edition, Springer-Verlag, pp. 234-235.
(18) Hewlett, E. L., Andrews, J. S. Jr., Ruffier, J., Schaefer III, F. W. (1982): Experimental infection of mongrel dogs with Giardia lamblia cysts and cultured trophozoites In: The Journal of infectious diseases, Vol. 145, No. 1, pp 89-93

The invention claimed is
1. A pharmaceutical formulation comprising nifurtimox and an anthelmintic comprising a cyclooctadepsipeptide.
2. A method of treating a disease caused by a Giardia species in an animal comprising administering to the animal in need thereof a pharmaceutical formulation comprising nifurtimox.
3. The method of claim 2, wherein the Giardia species is Giardia lamblia.
4. The method of claim 2, wherein the pharmaceutical formulation further comprises an anthelmintic.
5. The method of claim 4, wherein the anthelmintic comprises a cyclooctadepsipeptide.
6. The method of claim 5, wherein the cyclooctadepsipeptide comprises a compound selected from the group consisting of PF1022, PF1022A, PF1022-221, salts thereof, and solvates thereof.
7. The method of claim 2, wherein the pharmaceutical formulation comprising nifurtimox is administered orally to the animal.
8. The method of claim 7, wherein the pharmaceutical formulation comprising nifurtimox is a tablet.
9. The method of claim 7, wherein the pharmaceutical formulation comprising nifurtimox is administered to the animal by metering into the animal's feed or drinking water.
10. The method of claim 2, further comprising applying a disinfectant to a location where infectious feces is excreted by the animal during treatment.
11. A method of treating a disease caused by a Giardia species and a nematode infection in an animal comprising administering to the animal in need thereof a pharmaceutical composition comprising nifurtimox and an anthelmintic.
12. The method of claim 11, wherein the Giardia species is Giardia lamblia.

13. The method of claim 11, wherein the anthelmintic comprises a cyclooctadepsipeptide.

14. The method of claim 13, wherein the cyclooctadepsipeptide comprises a compound selected from the group consisting of PF1022, PF1022A, PF1022-221, salts thereof, and solvates thereof.

15. The method of claim 11, wherein the pharmaceutical formulation comprising nifurtimox is administered orally to the animal.

16. The method of claim 15, wherein the pharmaceutical formulation comprising nifurtimox is a tablet.

17. The method of claim 11, wherein the pharmaceutical formulation comprising nifurtimox is administered to the animal by metering into the animal's feed or drinking water.

18. The method of claim 11, further comprising applying a disinfectant to a location where infectious feces is excreted by the animal during treatment.

19. The pharmaceutical formulation of claim 1, wherein the cyclooctadepsipeptide comprises a compound selected from the group consisting of PF1022, PF1022A, PF1022-221, salts thereof, and solvates thereof.

20. The pharmaceutical formulation of claim 1, wherein the cyclooctadepsipeptide is emodepside, salt thereof, or solvate thereof.

* * * * *